(12) United States Patent
Abellatif et al.

(10) Patent No.: US 9,051,568 B2
(45) Date of Patent: Jun. 9, 2015

(54) ANTI-SENSE MICRORNA EXPRESSION VECTORS

(75) Inventors: Maha Abellatif, Morristown, NJ (US); Stephen F. Vatner, New York, NY (US); Dorothy E. Vatner, New York, NY (US); Junichi Sadoshima, Berkely Heights, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 365 days.

(21) Appl. No.: 12/989,627

(22) PCT Filed: Apr. 27, 2009

(86) PCT No.: PCT/US2009/041825
§ 371 (c)(1),
(2), (4) Date: Jan. 10, 2011

(87) PCT Pub. No.: WO2009/132351
PCT Pub. Date: Oct. 29, 2009

(65) Prior Publication Data
US 2011/0105592 A1 May 5, 2011

Related U.S. Application Data

(60) Provisional application No. 61/125,515, filed on Apr. 25, 2008, provisional application No. 61/206,953, filed on Feb. 6, 2009.

(51) Int. Cl.
*C07H 21/04* (2006.01)
*C12N 15/113* (2010.01)

(52) U.S. Cl.
CPC ........ *C12N 15/113* (2013.01); *C12N 2310/113* (2013.01); *C12N 2310/11* (2013.01); *C12N 2310/111* (2013.01); *C12N 2310/141* (2013.01)

(58) Field of Classification Search
CPC .................... C12N 2310/141; C12N 2310/11; C12N 2310/111; C12N 2310/113
See application file for complete search history.

(56) References Cited

U.S. PATENT DOCUMENTS

| | | | |
|---|---|---|---|
| 2003/0074684 A1 * | 4/2003 | Graham et al. | 800/278 |
| 2005/0064489 A1 * | 3/2005 | Zhang et al. | 435/6 |
| 2005/0182005 A1 * | 8/2005 | Tuschl et al. | 514/44 |
| 2005/0197310 A1 | 9/2005 | Mor et al. | 514/44 A |
| 2005/0244377 A1 | 11/2005 | Sigg et al. | 424/93.2 |
| 2005/0256072 A1 | 11/2005 | Aronin et al. | 514/44 A |
| 2005/0261218 A1 * | 11/2005 | Esau et al. | 514/44 |
| 2006/0185027 A1 * | 8/2006 | Bartel et al. | 800/14 |
| 2007/0224633 A1 | 9/2007 | Skerra et al. | 435/7.1 |
| 2007/0270579 A1 | 11/2007 | Jadhav et al. | 536/23.1 |

OTHER PUBLICATIONS

Spankuch et al. (J. Nat. Cancer Inst. 2004, 96(11):862-872.*
International Search Report from PCT/US2009/041825, Jul. 17, 2009.
International Preliminary Report on Patentability from PCT/US2009/041825, Oct. 26, 2010.

* cited by examiner

*Primary Examiner* — Jon E Angell
(74) *Attorney, Agent, or Firm* — Licata & Tyrrell P.C.

(57) ABSTRACT

The present invention relates to an alternative strategy for expressing the antisense sequence of a miRNA. This system allows for continuous production of the antisense sequence and subsequently complete knockdown of the targeted miRNA.

8 Claims, 14 Drawing Sheets

Figure 8 e-i
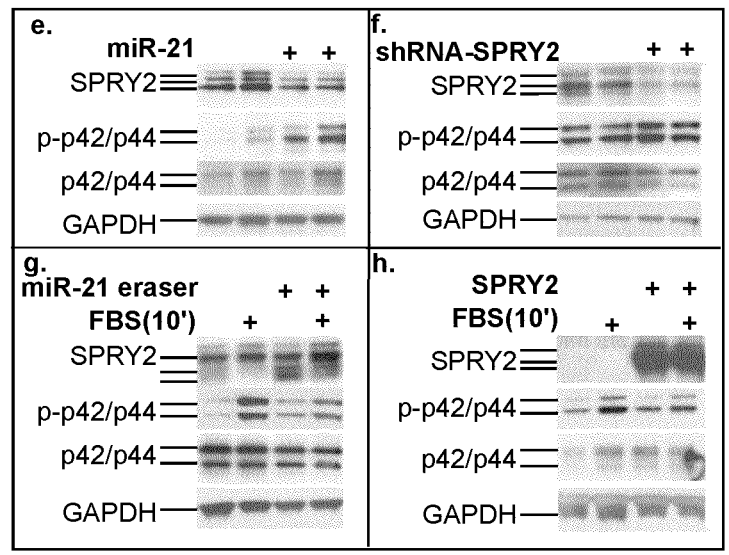
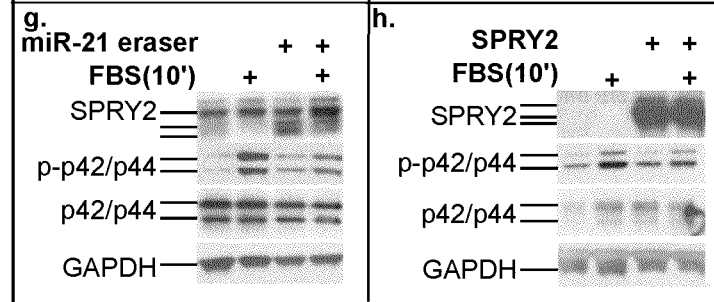

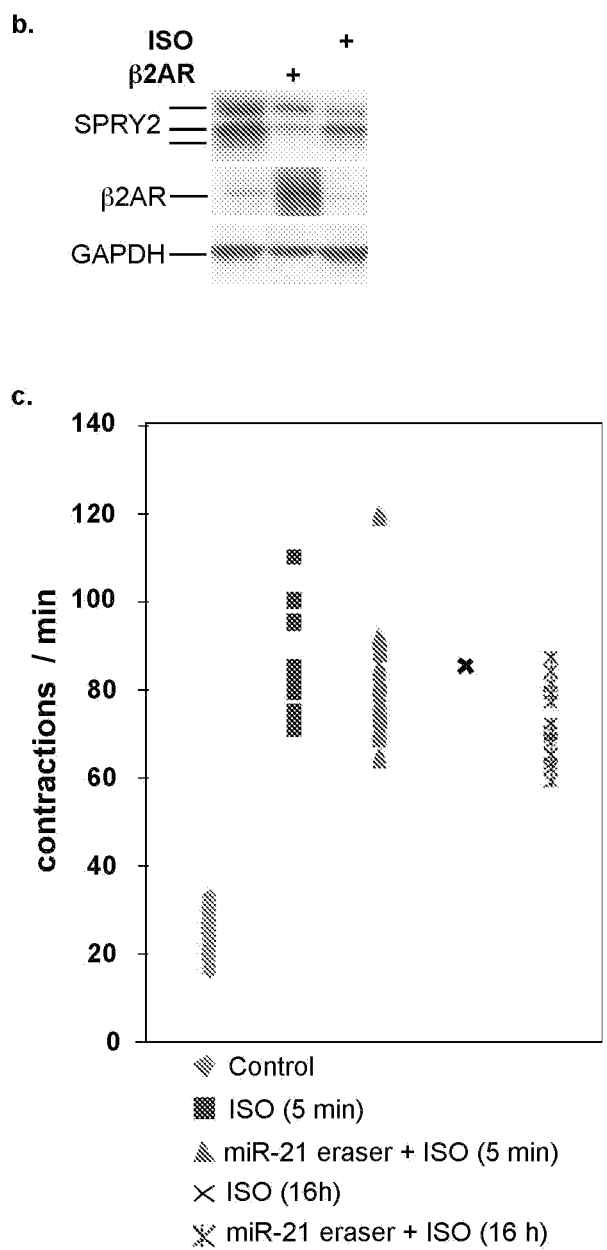
Figure 9 b-c

ANTI-SENSE MICRORNA EXPRESSION VECTORS

This application claims priority to U.S. Provisional Application Nos. 61/125,515, filed Apr. 25, 2008 and 61/206,953, filed Feb. 6, 2009, the disclosures of which are hereby incorporated by reference in their entireties for all purposes.

BACKGROUND OF THE INVENTION

MicroRNA (miRNA) are tiny posttranscriptional gene regulators, ~20 nt oligoribonucleotides, that are differentially expressed during various diseases, such as heart failure and cancer, and have been implicated in the underlying pathogenesis. Each has the potential to regulate a set of specific genes that are involved in a common cellular function. For example, an array of growth-promoting genes are targeted by miR-1, and require its downregulation at the onset of cardiac hypertrophy. Since miRNA levels are posttranscriptionally regulated, they, therefore, have the potential to elicit an immediate and specific change in translation by attaching to, or detaching from, mRNA targets. Thus, an increase or a decrease in a specific miRNA may underlie the mechanism of these diseases.

Although mammalian miRNAs are commonly known for inhibiting translation vs. inducing mRNA degradation, there is now substantial evidence to support the latter as well. Therefore, it is plausible that transient exposure of an mRNA to a targeting miRNA will inhibit its translation while chronic exposure will result in its degradation.

Antisense miRNA is a critical tool for understanding the functions of the different miRNAs. Designing an expression vector of choice enhances the spectrum of our studies in the different cell lines and tissues as well as animal models. For example, cardiac myocytes are poor candidates for transfection and uptake of the cholesterol-linked oligos, in addition, to having a non-specific response to the cholesterol itself. On the other hand, they have great affinity to adenoviral vectors. The expression vectors can also be used to create transgenic mice models as a much faster alternative means for creating a knockout of a specific miRNA.

One approach to target a specific miRNA of interest has been to develop antisense sequences and deliver them to the cells via lipid based transfection methods or by attaching a cholesterol moiety to the oligonucleotide to render it cell permeable. The latter may be delivered in vivo with some success and has the potential to be used as a therapeutic agent. But like anything else this approach has its limitations and alternatives for different applications are always necessary.

This invention relates to an alternative strategy in which the antisense sequence of an miRNA of interest was expressed through an expression vector using a specific design that would allow for successful expression of 20-40 nucleotide sequences. This expression cassette can be delivered via plasmid DNA or viral vectors for more efficient in vivo and in vitro delivery. This system allows for continuous production of the antisense sequence and subsequently complete knockdown of the targeted miRNA.

OBJECTS AND SUMMARY

Figure 1:
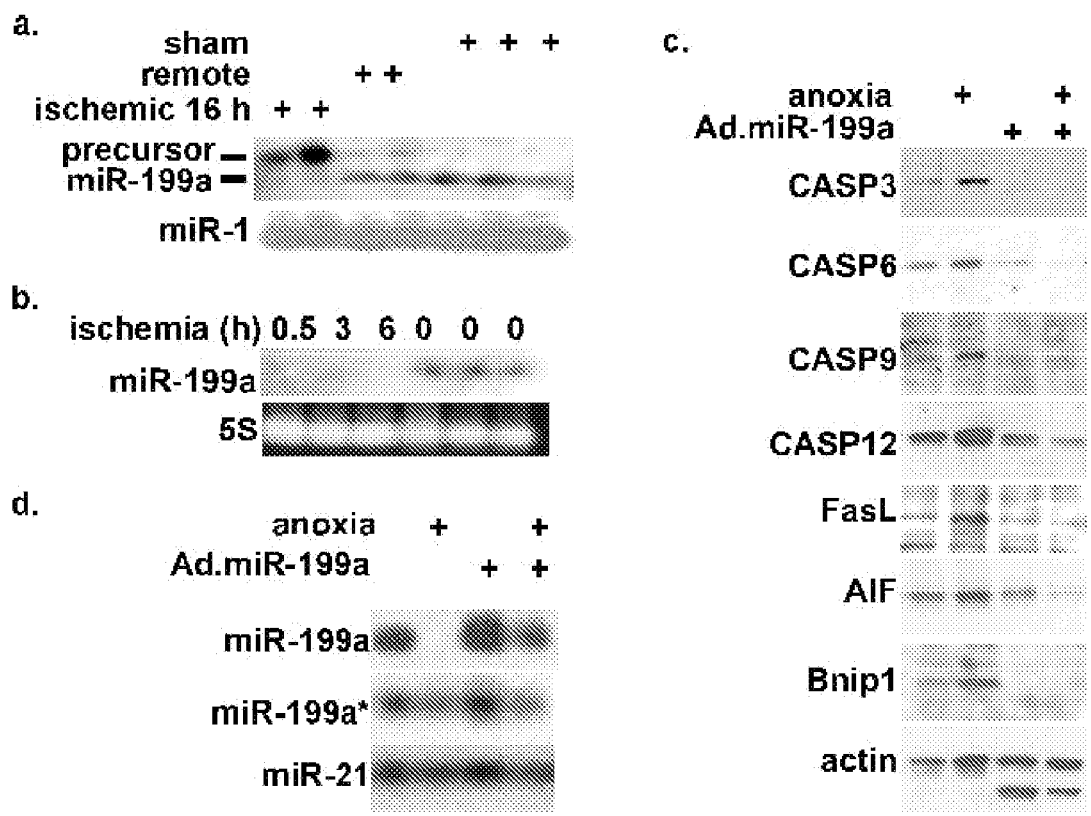
FIG. 1 shows downregulation of miR-199a is required for anoxia-induced proapoptotic genes.

The present invention is directed to certain miRNA and their antisense RNA that can be derivatized to a pharmaceutical acceptable form and used in the treatment of miRNA-related conditions.

In particular, the present invention is directed to the use of expressed antisense miRNA using plasmid or viral vectors.

In certain embodiments, the present invention is directed to the treatment of cardiovascular disease or heart failure using miRNA and their antisense RNA.

In other embodiments, the present invention is directed to the treatment of cancer using miRNA and their antisense RNA.

In certain embodiments, the present invention is directed to the use of miR-21 and its antisense RNA in the treatment of diseases associated with this particular miRNA.

In certain embodiments, the present invention is directed to the use of mi-R-199a and its antisense RNA in the treatment of diseases associated with this particular miRNA.

In certain embodiments, the present invention is directed to an expression vector comprising a double stranded DNA, wherein the double stranded DNA comprises DNA complements of at least two repeats of at least one sequence of antisense miRNA.

In other embodiments, the present invention is directed to a plasmid comprising the expression vectors described herein.

In yet other embodiments, the present invention is directed to a cell comprising the expression vectors described herein.

In certain embodiments, the present invention is directed to a method of inhibiting the expression of miRNA in a subject, comprising administering to the subject an expression vector comprising a double stranded DNA, wherein the double stranded DNA comprises DNA complements of at least two repeats of at least one sequence of antisense miRNA, wherein the antisense miRNA is complementary to the miRNA.

As used herein, the term "subject" includes any human or non-human animal. In some embodiments, the subject is a human. In further embodiments, the subject is a rodent or a primate.

The above and still further objects, aspects, features and attendant advantages of the present invention will be better understood from a consideration of the following detailed description of the invention as represented by certain preferred methods and embodiments thereof, taken in conjunction with the accompanying drawings.

DETAILED DESCRIPTION

Cardiac hypertrophy is characterized by a change in the gene expression pattern that recapitulates the neonatal profile. This switch is triggered by transcriptional and post-transcriptional regulators. Several labs have recently reported an array of post-transcriptional miRNA regulators that are differentially expressed and play a role in the development of cardiac hypertrophy. The underlying mechanisms involved in cardiac hypertrophy are reminiscent of those employed in cancer, overlapping in many growth promoting molecules and pathways.

One such miRNA is the post-transcriptional regulator miR-21, which is upregulated in many forms of cancer, as well as, during cardiac hypertrophic growth. Its knockdown activates caspases and induces apoptosis in glioblastoma cells and sensitizes cholangiocytes to chemotherapeutic agents, while its over-expression inhibits apoptosis in myeloma cells. miR-21 is shown to target and down-regulate the expression of the tumor suppressors tropomyosin 1, phosphatase and tensin homolog (PTEN), and programmed cell death 4 (Pdcd4) and promote cell invasion and metastasis. Moreover, anti-miR-21 inhibits tumor growth in vivo and in vitro. In human colorectal cancer the levels of miR-21 positively correlated with the development of metastasis but not tumor size. Most interestingly, out of 37 differentially expressed miRNA (26 upregulated and 11 down-regulated) in colon adenocarcinoma, upregulation of miR-21 singularly correlated with lower survival rates and poor response of patients to therapy. Thus, miR-21 is poised to be a major therapeutic target in colon carcinoma.

To understand its roll, miR-21 was over-expressed in cardiocytes where it revealed a unique type of cell-to-cell 'linker' in the form of long slender outgrowths/branches. miR-21 directly targets and down-regulates the expression of sprouty2 (SPRY2), an inhibitor of branching morphogenesis and neurite outgrowths. β-adrenergic receptor (βAR) stimulation induces upregulation of miR-21 and down-regulation of SPRY2 and is, likewise, associated with connecting cell branches. Knockdown of SPRY2 reproduced the branching morphology in cardiocytes, and vice versa, knockdown of miR-21 using a specific 'miRNA eraser' or over-expression of SPRY2 inhibited βAR-induced cellular outgrowths. These structures enclose sarcomeres and connect adjacent cardiocytes through functional gap junctions. To determine how this aspect of miR-21 function translates in cancer cells, it was knocked down in colon cancer SW480 cells. This resulted in disappearance of their microvillus-like protrusions, which was reproduced by over-expression of SPRY2. Thus, an increase in miR-21 appears to be involved in the formation various forms of cellular protrusions through directly targeting and down-regulating SPRY2.

In addition to miR-21, the present inventors have discovered that miR199a is acutely downregulated in cardiac myocytes upon a decline in oxygen tension. Early ischemia or hypoxia preconditioning (IPC or HPC) is an immediate cellular reaction to brief hypoxia/reoxygenation cycles that involves de novo protein, but not mRNA, synthesis. It was first described as a mechanism that protected the heart against subsequent prolonged ischemia- or ischemia/reperfusion (I/R)-induced damage. It is mediated, at least in part, by adenosine, which is produced upon hydrolysis of ATP, and released from the cell to stimulate a surface receptor. Central to early preconditioning effects is the protection of mitochondria against hypoxic damage, mainly through inhibiting the opening of MPTP. PKCε has been shown to interact with the MPTP proteins and inhibit mitochondrial swelling, possibly through a GSK3β-mediated effect.

Hif-1α is a well-established transcription factor that is rapidly induced by hypoxia through a posttranscriptional mechanism, in all tested cell types. It accounts for the transcription of 89% of genes that are upregulated during hypoxia. In the heart, overexpression of Hif-1α during hypoxia resulted in a smaller infarct size following ischemia/reperfusion and was associated with higher capillary density, VEGF, and iNOS, in the peri-infarct zone. This suggested that Hif-1α plays a role in late IPC. Recently, a study showed that mice heterozygous for Hif-1α fail in early preconditioning, while it was also reported that knockdown of Hif-1α abolished the effect of early ischemia preconditioning. But the mechanism of Hif-1α-mediated early preconditioning remains unexplained.

Replenishing miR199a during anoxia inhibits Hif-1α expression and its stabilization of p53, and, thus, reduces apoptosis. On the other hand, knockdown of miR-199a during normoxia results in the upregulation of Hif-1α and Sirtuin 1 (Sirt1) and reproduces hypoxia preconditioning. Sirt1 is also a direct target of miR-199a and is responsible for down-regulating prolyl hydroxylase 2 (PHD2), required for stabilization of Hif-1α.

Thus, it is concluded that miR-199a is a master regulator of a hypoxia-triggered pathway and can be exploited for preconditioning cells against hypoxic damage. In addition, the data demonstrate a functional link between two key molecules that regulate hypoxia preconditioning and longevity.

Expressing the antisense sequences of miRNAs, such as miR-21 and miR-199a can therefore be a valuable tool in the treatment of related diseases. The advantage of one of the embodiments of the present invention, expressing antisense miRNA using plasmid or viral vectors, is compared to currently available technologies in the table below.

TABLE 1

|  | Expressed antisense microRNA using plasmid or viral vectors | Modified non-hydrolysable antisense microRNA | Modified non-hydrolysable antisense microRNA with end-linked cholesterol |
|---|---|---|---|
| Cost | Cost effective large scale amplification of plasmid or viral vectors in the lab | Requires continued costly oligo synthesis | Requires continued very costly oligo synthesis |
| Cell specificity | A choice of plasmid transfection or viral | Limited to cells that can be efficiently | Cell permeability is dictated by the cell |

TABLE 1-continued

|  | Expressed antisense microRNA using plasmid or viral vectors | Modified non-hydrolysable antisense microRNA | Modified non-hydrolysable antisense microRNA with end-linked cholesterol |
|---|---|---|---|
|  | vector that will accommodate any cell type | transfected with naked DNA or RNA, which excludes cardiac and skeletal muscle cells. | membrane composition. |
| Mode of delivery | A choice of plasmid transfection or viral transduction | Transfection | The reagent is cell permeable |
| Bioavailability | Continuous expression. The plasmid may be stably transfected into cells or using viral vectors that integrate into the genome. | Although the oligo is non-hydrolysable, it will be diluted out in proliferating cell types | Although the oligo is non-hydrolysable, it will be diluted out in proliferating cell types |
| Applicability | In vivo and in vitro studies including transgenic animal models | In vitro studies | In vivo and in vitro studies not including transgenic models |
| Design advantage | 1. Unmodified antisense that is continuously produced and ideal for pairing with the target.<br>2. Uses a U6 promoter with defined start and stop sites | Modified antisense that may not pair as efficiently with the target miRNA. | Modified antisense and a bulky cholestryl moiety at one end that may not pair as efficiently with the target miRNA |

EXAMPLES

Example 1

Vector Creation

Two repeats of a specific antisense microRNA sequence is synthesized as a double strand DNA with ApaI- and HindIII restriction site-compatible overhangs at the 5' and 3' ends respectively.

In addition, at the end of the antisense sequence 6 deoxythymidine residues are added, which is a stop signal for RNA polymerase III.

This double strand DNA is cloned downstream of a U6 RNA polymerase III-dependent promoter (Ambion) in the plasmid vector pDC311 (from Microbix). This plasmid can be used as such, or delivered to the cells via a lipid-based transfection method.

In an additional step, the plasmid was cloned it into recombinant adenovirus serotype 5 (Microbix) for efficient delivery in cardiac myocytes both in culture and in vivo.

Example 2

MiR-199a

Downregulation of MiR-199a During Anoxia is Required for Induction of Proapoptotic Genes Results of studies regarding differentially expressed miRNA in the heart, shown in FIG. 1 wherein:

a. C57Bl/6 mice were subjected to left coronary artery occlusion for 16 h. The ischemic and remote regions of the left ventricle, and the sham-operated ventricle, were isolated and total RNA was extracted and analyzed by Northern blotting (n=3).

b. Mice were subjected to left coronary artery occlusion for 0.5, 3, and 6 h and analyzed as in (a).

c. Myocytes were infected with a control or miR199a-expressing adenoviruses before exposure to anoxia for 24 h in complete culture medium with serum (where marked by +). Protein was extracted and analyzed by Western blotting (n=3).

d. Myocytes were treated as in (c). Total RNA was extracted and analyzed by Northern blotting (n=3), revealed that mature miR199a was reduced to undetectable levels during cardiac ischemia, while its precursor continued to accumulate (FIG. 1a). A time course revealed that this occurred as early as 30 minutes after ischemia (FIG. 1b). To investigate its function, it was over-expressed in myocytes exposed to anoxia. Western blot analysis revealed that miR-199a resulted in complete inhibition of anoxia-induced caspase-3, -6, -9, 12, FasL, AIF, and Bnip1 (FIG. 1c). While Northern blots analysis showed that miR-199a, but not miR199a* or miR-21, was completely abolished by anoxia and that the adenoviral delivered construct was able to rescue this downregulation (FIG. 1d). This suggested that miR-199a downregulation is required for upregulation of hypoxia-induced apoptotic genes.

MiR-199a Targets and Inhibits Hif-1α

Figure 2:
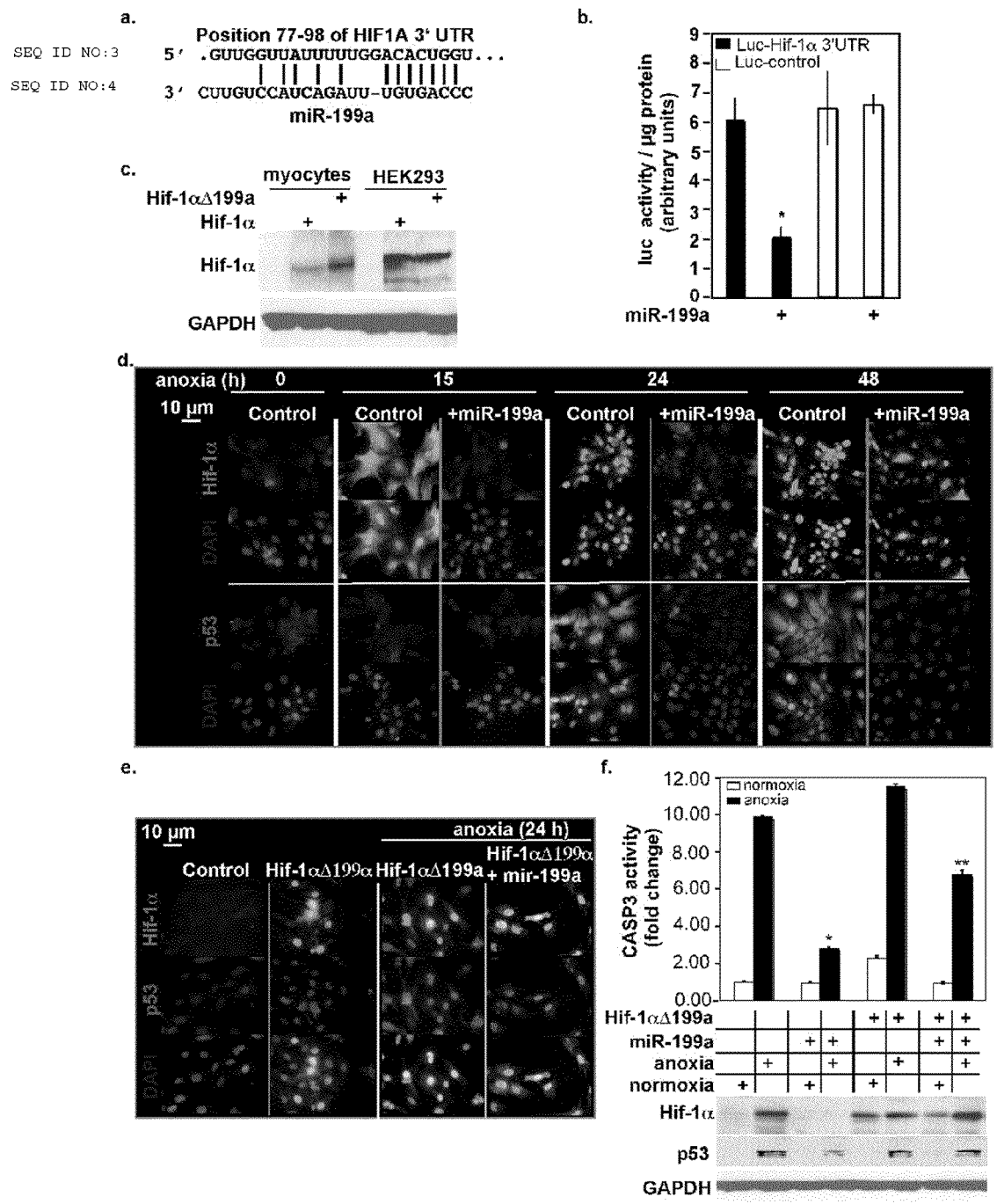
FIG. 2 shows MiR-199a targets and inhibits Hif-1α.

Results are shown in FIG. 2 wherein:

a. The alignment between mus musculus miR-199a and the 3'UTR of HIF1A, identified by TargetscanS software.

b. The miR-199a target region, or a mutant, was cloned into the 3'UTR of a luciferase gene (represented in the graph by black and white bars, respectively). These constructs were delivered to myocytes via adenovirus, in addition to exogenous miR-199a (where marked by +) or a control virus (n=6). After 24 h luciferase activity was measured, averaged, and plotted. The y-axis represents arbitrary luciferase activity normalized to µg protein content. Error bars represent standard error of the mean (SEM) and *=p<0.01, miR-199a treated luciferase-Hif-1α 3'UTR target vs. control.

c. Wild type Hif-1α cDNA or a mutant lacking miR199a target site (Hif-1 αΔ199a) were delivered to cardiac myocytes or HEK293 cells. After 24 h protein was extracted and analyzed by Western blotting (n=2).

d. Myocytes were plated on gelatin-coated glass chamber slides. They were then treated with a control or a miR-199a overexpressing virus for 24 hr before subjecting them to various periods of anoxia as indicated on the top of each panel. Parallel slides were stained separately with anti-Hif-1α (green) or anti-p53 (red) antibodies, and DAPI (blue) (n=4).

e. Myocytes were cultured as in (d.) and treated with a control or Hif-1 αΔ199a virus, in absence or presence of a control or miR-199a virus for 24 h. Cells were then exposed to anoxia for an additional 24 h where indicated, before they were fixed and co-stained with anti-Hif-1α (green), anti-p53 (red), and DAPI (blue) (n=3).

f. Myocytes were treated as in (e.). Protein was extracted and either assayed for caspase 3 activity (graph, n=6) or analyzed by Western blotting (n=3). The treatments are indicated in the grid below the graph by + signs and each aligned with its Western blot results. Results were averaged, normalized to protein content, and plotted as fold change after adjusting basal levels to 1. Error bars represent SEM, *=p<0.001 miR-199a-treated vs. untreated cells during hypoxia, **=p<0.01 miR-199a-treated plus Hif-1aΔ199a vs. miR-199a-treated.

Computational analysis predicted that Hif-1α is a miR-199a target. FIG. 2a shows the alignment between miR-199a and a highly conserved region within the 3'UTR of mouse Hif-1α. Inclusion of the target sequence within the 3'UTR of a luciferase gene rendered it a target of miR-199a, as demonstrated by the inhibition of its activity upon overexpression of miR-199a (FIG. 2b). For further confirmation, the Hif-1α cDNA was cloned with or without a deletion of its miR-199a recognition site. The deletion resulted in ~4x higher expression of the Hif-1α protein in cardiac myocytes, but not in HEK293 cells that are devoid of endogenous miR-199a (FIG. 2c). The data demonstrate that miR-199a directly targets and inhibits Hif-1α.

To determine the effect of miR-199a on endogenous Hif-1α, its stabilization of p53, and myocyte apoptosis during anoxia, the myocytes were subject to anoxia in the absence or presence of excess miR-199a. FIG. 2d shows that Hif-1α is robustly induced within 15 h of oxygen deprivation. Initially Hif-1α is seen throughout the cell, but upon longer periods of anoxia it becomes more restricted to the nucleus and coincides with the increase in p53 after 24 h. Overexpression of miR-199a completely abolished Hif-1α and p53 during the first 24 h of anoxia, but started losing effectiveness after 48 h. The results suggest that downregulation of miR-199a during anoxia is required for upregulation of Hif-1α and stabilization of p53.

Unlike Hif-1α, p53 is not a direct target of miR-199a, but has been shown to require Hif-1α for its stabilization during hypoxia. To test this possibility in cultured myocytes, myocytes were supplemented with Hif-1α lacking the miR-199a responsive element (Hif-1αΔ199a, FIG. 2e). This sustained the levels of Hif-1α during anoxia after overexpression of miR-199a, and completely rescued the downregulation of p53 (FIGS. 2e and 2f). The results confirm that p53 is not a direct target of miR-199a and that it requires Hif-1α for its stability during prolonged periods of anoxia. The expression levels of p53 positively correlated with caspase 3 activity in these cells, which was dramatically reduced by miR199a, but partially rescued by Hif-1αΔ199a (FIG. 2f). Therefore, the results suggest that downregulation of miR-199a is required for induction of hypoxia-induced apoptosis, at least partly, through the Hif-1αp53 pathway.

Knockdown of miR-199a Recapitulates Hypoxia Preconditioning

Figure 3:
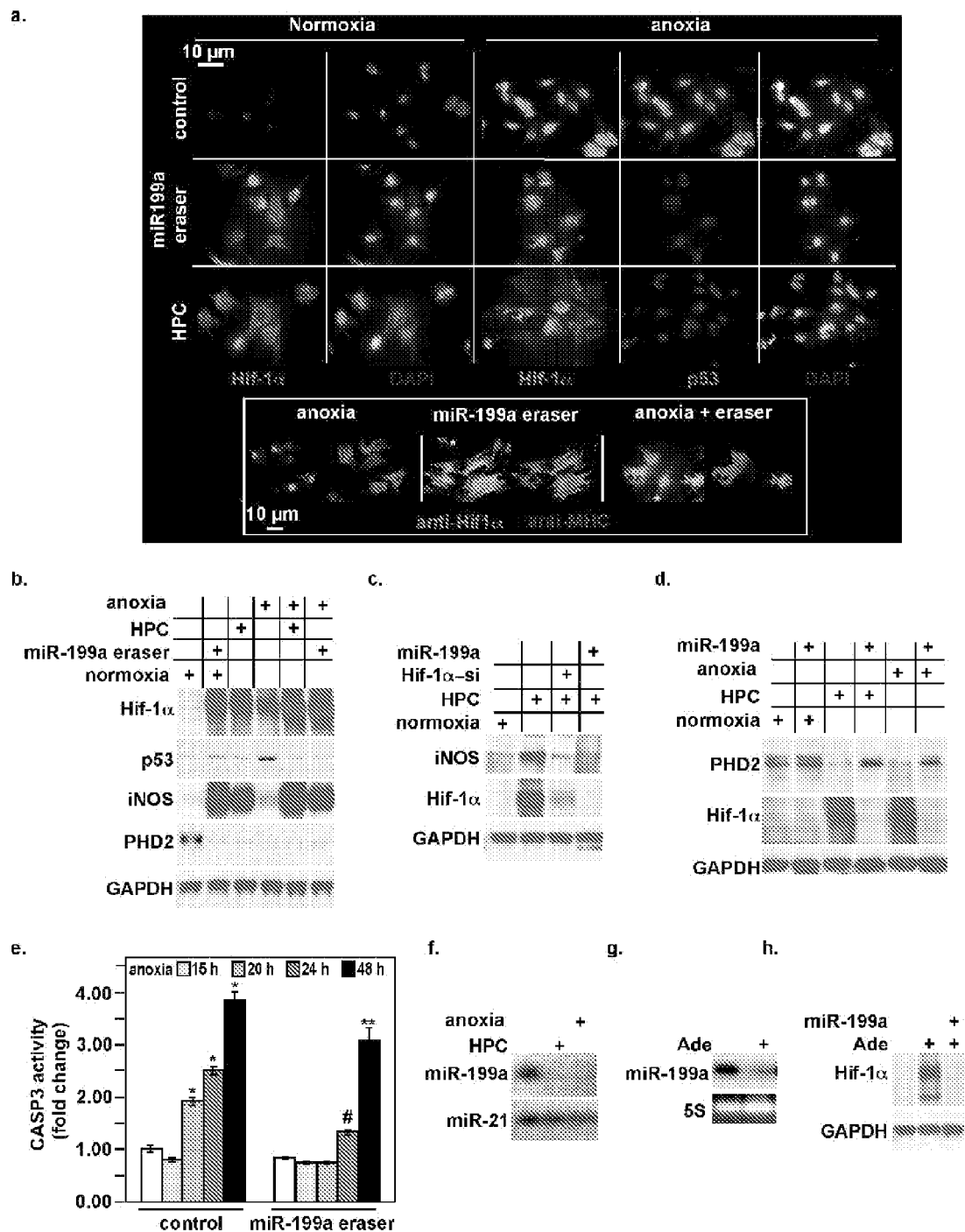
FIG. 3 shows Knockdown of miR-199a induces upregulation of Hif-1α, iNOS, and downregulation of PHD2, mimicking hypoxia preconditioning.

It was postulated whether knockdown of miR-199a during normoxia is sufficient for induction of Hif-1α as shown in FIG. 3 wherein:

a. Cardiac myocytes plated on gelatin coated glass chamber slides were treated with a control or miR-199a eraser-expressing adenovirus for 24 h, or HPC, as indicated on the left. A parallel set of myocytes were similarly treated and subsequently subjected to anoxia for 24 h, as indicated on the top. Myocytes were then fixed and co-stained with anti-Hif-1α (green), anti-p53 (red), and DAPI (blue) (n=5). The lower set of panels show myocytes exposed to anoxia for 24 h, miR-199a eraser, or hypoxia+eraser, as indicated. Cells were co-stained with a rabbit polyclonal anti-Hif-1α and anti-myosin heavy chain (MHC, red) (n=2).

b. Myocytes were treated as described in (a.) and as indicated in the grid by + signs. Protein was extracted and analyzed by Western blotting (n=3).

c. Myocytes were subjected to HPC before or after pretreatment with a control, miR-199a-, and Hif-1α short interfering RNA (Hif-1α-si)-expressing adenoviruses for 24 h, where indicated by + signs. Protein was extracted and analyzed by Western blotting for the molecules indicated on the left.

d. Myocytes were subjected to 24 h anoxia or HPC, before or after treatment with a control or miR-199a-expressing virus for 24 h where indicated by + signs. Protein was extracted and analyzed by Western blotting for the molecules indicated on the left.

e. Myocytes were subjected to 15, 20, 24, or 48 h anoxia before or after treatment with a control or miR-199a eraser for 24 h, as indicated. Protein was extracted and assayed for caspase 3 activity (n=6). Results were averaged, normalized to protein content, and plotted as fold change, after adjusting basal levels to 1. Error bars represent SEM, *=p<0.01 anoxia vs. normoxia; #=p<0.01 miR-199a eraser-pretreated plus 24 h anoxia vs. control-treated plus 24 h anoxia; **=p<0.5 miR-199a eraser-pretreated plus 48 h anoxia vs. control-treated plus 48 h anoxia.

f. Myocytes were subjected to HPC or 24 h anoxia as indicated with the + sign. Total RNA was then extracted and analyzed by Northern blotting for the miRNA indicated on the left (n=2).

g. Myocytes were stimulated with 100 µM adenosine for 16 h. Total RNA was then extracted and analyzed by Northern blotting for the miRNA indicated on the left (n=2).

h. Myocytes were treated as in (g). Protein was extracted and analyzed by Western blotting (n=2).

FIG. 3a shows that abrogation of miR-199a with an antisense miR-199a expression vector (miR-199a eraser) resulted in the upregulation of Hif-1α. Interestingly, its distribution favored the cytosol, where it was punctate in appearance, similar to that observed during HPC, and in contrast to its predominant nuclear localization seen during anoxia. Moreover, HPC or miR-199a knockdown inhibited hypoxia-induced Hif-1α transport to the nucleus, as well as, upregulation of p53. In the lower panels it is demonstrated that miR-199a eraser-induced upregulation of Hif-1α occurs in myosin heavy chain (MHC)-positive myocytes, which proves that miR-199a is intrinsic to these cells.

Results of the immunostaining were confirmed by Western blot analysis (FIG. 3b). In addition, it is shown that HPC and miR-199a knockdown, but not anoxia, were associated with robust upregulation of iNOS. Pretreatment of cells with HPC or miR-199a eraser provided cells with iNOS during anoxia and inhibited upregulation of p53. iNOS expression was dependent on downregulation of miR-199a and upregulation of Hif-1α, as it was abolished by overexpression of miR-199a during HPC or by Hif-1α knockdown (FIG. 3c).

MiR-199a eraser-induced upregulation of Hif-1α during normoxia suggested that it might be associated with inhibition or downregulation of prolyl hydroxylase 2 (PHD2). Indeed, PHD2 was reduced more than 90% in eraser-treated cells and during HPC or anoxia (FIG. 3b). This decrease was reversed by overexpression of miR-199a, suggesting that it requires downregulation of the miRNA under these conditions (FIG. 3d). Not only did the miR-199a eraser elicit a gene expression pattern that mimicked HPC, but it also retarded the increase in caspase-3 activity induced by anoxia (FIG. 3e).

The above results suggest that downregulation of miR-199a might be a mediator of HPC. As observed in FIG. 3f, miR-199a, but not miR-21, was rendered undetectable by HPC. Moreover, adenosine, an established mediator of ischemia preconditioning (IPC), induced miR-199a downregulation (FIG. 3g). This was associated with upregulation of Hif-1α that was blocked by overexpression of miR-199a (FIG. 3h). This suggests that HPC or IPC require downregulation of miR199a.

Hif-1α Associates with and Protects Mitochondria During HPC

Figure 4:
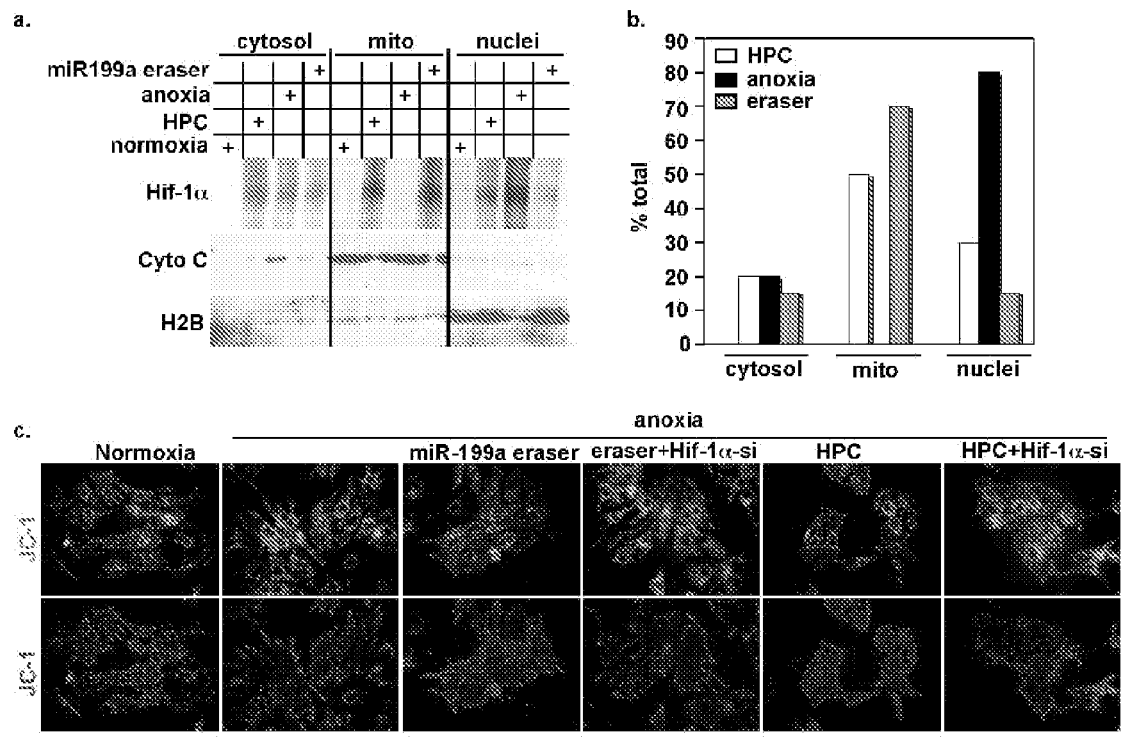
FIG. 4 shows Hif-1α associates with mitochondria and is required for HPC-mediated protection.

As noted earlier, during preconditioning of cells with hypoxia or miR-199a eraser, Hif-1α exhibited a punctate appearance in the cytosol. Since mitochondrial protection is central to preconditioning, it was questioned whether Hif-1α might associate with this organelle as shown in FIG. 4 wherein:

a. Cardiac myocytes were subjected to HPC, 24 h anoxia, or treated with a control or the miR-199a eraser-expressing virus for 24 h, as indicated in the grid by + signs. Cells were fractionated into cytosol, mitochondria, and nuclei and analyzed by Western blotting for the proteins indicated on the left (n=3).

b. The Hif-1α signal shown in (a.) was quantitated in all fractions, for each treatment, and the % of total was calculated and plotted (n=3).

c. Cardiac myocytes were plated on gelatin-coated glass chamber slides. Cells were treated with a control or a Hif-1α-si-expressing adenovirus for 48 h before applying miR-199a eraser or HPC. They were then exposed to anoxia for 24 h. Following that, JC-1 dye was applied and the cells imaged live (n=4).

The results revealed that Hif-1α co-purifies with mitochondria during HPC or miR-199a eraser treatment of cells, but was undetectable in that fraction after 24 h anoxia (FIG. 4a). On the other hand, there was more nuclear Hif-1α during the latter condition than was observed during preconditioning (FIG. 4b).

To determine whether miR-199a eraser treatment protects against hypoxia-induced mitochondrial damage and if it requires Hif-1α, mitochondrial integrity was monitored using the JC-1 dye. FIG. 4c shows that hypoxia-induced mitochondrial damage was rescued by HPC or miR-199a eraser pretreatment. This is reflected by low levels of green florescent monomeric dye in the cytosol and higher levels of red florescent aggregates in intact healthy mitochondria and vice versa during anoxia. Knockdown of Hif-1α abrogated the mitochondrial protective effect of preconditioning. Thus, Hif-1α is required for mitochondrial protection during preconditioning, plausibly mediated through a mechanism that involves a direct interaction.

MiR-199a Targets Sirt1

Figure 5:
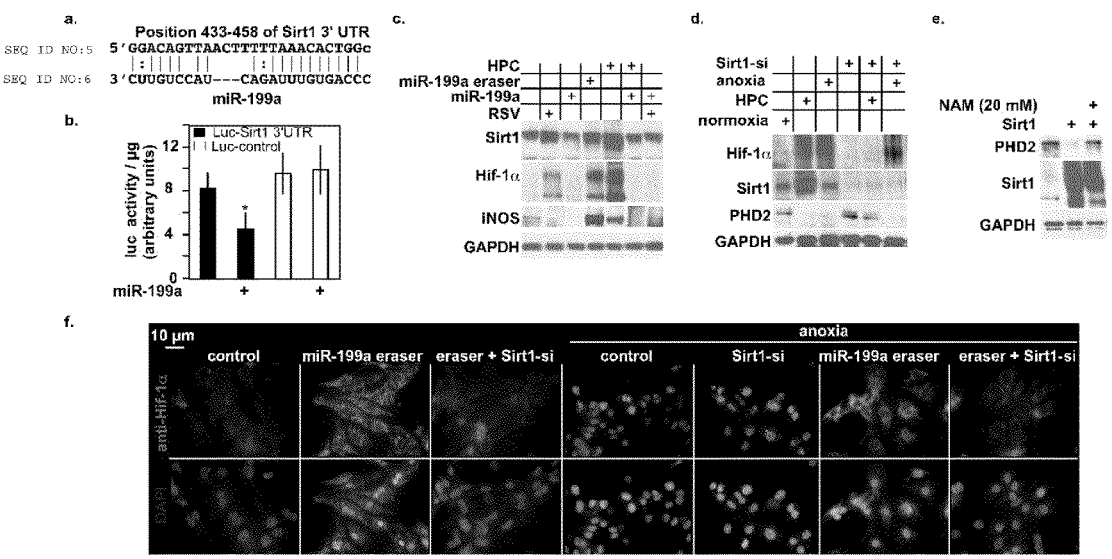
FIG. 5 shows Sirt1 is a direct target of miR-199a, is upregulated during HPC, and is required for downregulation of PHD2.

Intriguingly, Sirt1, a class III histone deacetylase and a longevity gene, is another miR-199a predicted target as shown in FIG. 5 wherein:

a. The alignment between *mus musculus* miR-199a and a 3'UTR region of Sirt1.

b. The miR-199a target site, or a mutant, was cloned into the 3'UTR of a luciferase gene (represented in the graph by black and white bars, respectively). These constructs were delivered to myocytes via adenovirus, in addition to exogenous miR-199a (where marked by +) or a control virus (n=6). After 24 h, luciferase activity was measured, averaged, and plotted. The y-axis represents arbitrary luciferase activity normalized to μg protein content. Error bars represent standard error of the mean (SEM) and *=p<0.01, miR-199a-treated, luciferase-Sirt13'UTR target vs. control.

c. Myocytes were treated with 40 μM resveratrol (RSV) for 24 h or HPC, with or without exogenous miR-199a for an additional 24 h, or with miR-199a eraser for 24 h, where indicted by + signs (n=3). Protein was then extracted and analyzed by Western blotting.

d. Myocytes were treated with Sirt1-short interfering RNA (Sirt1-si) adenovirus for 48 h. These cells were then exposed to anoxia for 24 h or HPC, where indicated by + signs. Protein was then extracted and analyzed by Western blotting (n=3).

e. Myocytes were treated with a control or Sirt1-overexpressing virus in the absence or presence or 20 mM nicotinamide (NAM). Protein was extracted and analyzed by Western blotting (n=3).

f. Myocytes were plated on gelatin-coated glass chamber slides. Cells were treated with a control, miR-199a eraser, or a Sirt1-si-expressing adenovirus for 48 h, followed miR-199a eraser. A parallel set of similarly treated slides was then exposed to 24 h anoxia, as indicated above. Cells were then fixed and stained with anti-Hif-1α (green) and DAPI (blue) (n=3).

FIG. 5a shows a conserved alignment between the 2 molecules. Inclusion of this target sequence within the 3'UTR of a luciferase gene rendered it a target of miR-199a, as demonstrated by the inhibition of its activity upon overexpression of miR-199a, relative to a mutant sequence (FIG. 5b). In concordance, overexpression of miR-199a reduced endogenous Sirt1 by 50%, whereas its knockdown enhanced its expression 2.2× (FIG. 5c). This suggested that Sirt1 should increase during HPC as a result of the reduction in miR-199a. It was found that this was indeed the case, where Sirt1 was upregulated 9× after HPC and was completely reversed by replenishing miR-199a. But unlike Hif-1α, there was no increase in Sirt1 during anoxia (see FIGS. 5d and f). An increase in Sirt1 by resveratrol was also inhibited by overexpression of miR-199a and was associated with upregulation of Hif-1α. The results suggest that Sirt1 plays a role during HPC but not anoxia.

Sirt1 Induced Downregulation of PHD2 is Required for Hif-1α Accumulation

To examine the role of Sirt1 during HPC a loss-of-function approach was used. Unexpectedly, knockdown of Sirt1 resulted in loss of Hif-1α (FIG. 5d). This led us to speculate that Sirt1 may be regulating Hif-1α expression through regulating PHD2. Western blot analysis shows that the downregulation of PHD2 during HPC was blocked by the loss of Sirt1.

On the other hand, Sirt1 did not increase during anoxia nor did its knockdown influence upregulation of Hif-1α or downregulation of PHD2. Thus, Sirt1 is necessary for ablation of PHD2, but only during HPC. To determine whether it is sufficient, wild type Sirt1 was overexpressed in myocytes. The results of this experiment show >90% knockdown of PHD2 that was reversed by 20 mM nicotinamide (NAM), which inhibits the NAD-dependent deacetylase activity of Sirt1 (FIG. 5e). In addition, Sirt1 knockdown inhibited eraser-induced Hif-1α (FIG. 5f). Conversely, anoxia-induced Hif-1α, which is predominantly nuclear, was unaffected, except when the cells were pretreated with miR-199a eraser first. Thus, Sirt1 is necessary during HPC, and sufficient, for downregulating PHD2, and the effect is dependent on its deacetylase activity.

MiR-1.99a is Downregulated During IPC in Porcine Hearts

Figure 6:
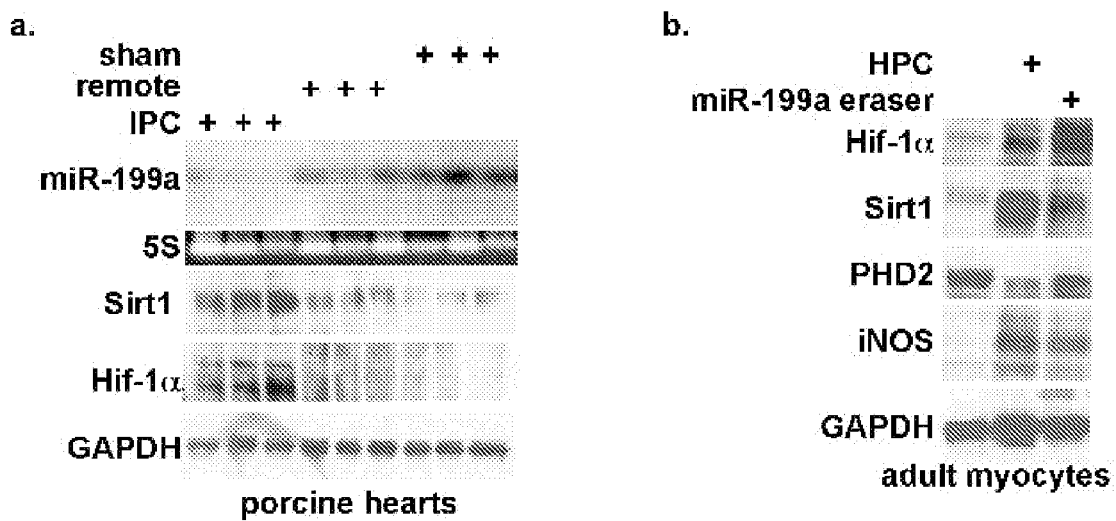
FIG. 6 shows MiR-199a is downregulated during IPC in porcine hearts and is associated with upregulation of Hif-1α and Sirt1.

Lastly, it was examined whether miR-199a, Hif-1α, and Sirt1 are regulated during early IPC in vivo as shown in FIG. 6 wherein:

a. Porcine hearts were preconditioned via 2×10 minute cycles of ischemia/reperfusion of the left ventricle (n=3). A second set of animals was subjected to a sham operation. The IPC area of the left ventricle, remote zone, and sham-operated ventricles, were immediately dissected (early/first window IPC) and analyzed by Northern and Western blotting. The top 2 panels are the results of a Northern blot and the lower 3 panels are Western blots.

b. Cultured adult rat cardiac myocytes were treated with miR-199a eraser for 24 h or HPC. Protein was extracted and analyzed by Western blotting for the molecules indicated on the left of each panel (n=3).

For that purpose IPC was induced in porcine hearts and analyzed the tissue by Northern and Western blots. FIG. 6a shows that miR-199a was reduced to undetectable levels in the preconditioned area of the heart, while the remote area exhibited modest downregulation of miR-199a, relative to a sham operated heart. This was associated with upregulation of Hif-1α and Sirt1, as predicted. Moreover, when knocked down in isolated adult rat myocytes, miR-199a derepressed Hif-1α and Sirt1 expression, proving that miR-199a is intrinsic to adult myocyte (FIG. 6b).

The results unveil a unique aspect of miRNA function: serving as molecular switches that trigger an immediate change in gene expression in response to a stimulus. Here it is shown that miR-199a is sensitive to low oxygen levels and is rapidly degraded and reduced to undetectable levels, thereby, releasing mRNA targets from its inhibitory effect. It was concluded that this was a posttranscriptional event, since it did not affect miR-199a*, which is expressed from the same stem-loop precursor. It is also shown that it was not a generalized effect, as there no changes observed in miR-21 or miR-1. Moreover, after longer periods of anoxia or ischemia, miR-199a precursor started to accumulate, suggesting that its transcription and primary transcript processing were unaffected by hypoxia. On the other hand, processing of the stem-loop precursor was inhibited. There is indeed accumulating evidence that miRNAs are widely regulated by posttranscriptional events. Our data further suggest that selective miRNA stability and processing of the stem-loop are subject to regulation in response to external stimuli. The question remains, though, as to what proteins are involved in the specific stabilization, or degradation, of miR-199a.

Hif-1α is the 'master transcriptional regulator' of hypoxia-induced gene expression. It is regulated by a posttranscriptional oxygen-sensitive mechanism that triggers its prompt expression upon a drop in oxygen levels. Prolyl hydroxylases (PHDs) hydroxylate Hif-1α during normoxia, which allows von Hippel-Lindau (VHL) to bind and ubiquitinate Hif-1α, marking it for proteasomal degradation. This process is inactivated during hypoxia, thus, permitting rapid accumulation of Hif-1α. Our results introduce miR-199a as an obligatory regulator of this process. It is shown that miR-199a directly targets and inhibits translation of Hif-1α mRNA during normoxia. This not only ensures suppression of Hif-1α during normoxia, but also circumvents the need for perpetual energy consumption required for its proteosomal degradation. Conversely, downregulation of miR-199a is required for upregulation of Hif-1α during hypoxia or HPC. But when miR-199a were knocked down during normoxia, it was not expected that it would be sufficient for inducing Hif-1α expression, since this would also require inhibition of PHD2. Surprisingly, a robust increase in its protein was observed, which indicated that miR-199a effects were mediated through a broader range of targets.

PHD2 is the primary prolyl hydroxylase family member that hydroxylates Hif-1α during normoxia. PHDs in general require O2, 2-oxoglutarate, and ascorbic acid for their full catalytic activity, and, thus, the availability of these factors regulates their function. On the other hand, the regulation of PHD2 protein availability during hypoxia has not been reported. In cardiac myocytes the level of PHD2 during hypoxia remains unexamined. Our results show that HPC or anoxia induces downregulation of PHD2 in cardiac myocytes, which is dependent on the reduction in miR-199a levels. Unexpectedly, it was discovered that Sirt1 is a direct target of miR-199a and mediates downregulation of PHD2 during HPC, through a NAD-dependent deacetylase function. Although there are no prior reports on its involvement in hypoxia or HPC, its activator, resveratrol, was reported to mediate preconditioning of the heart, brain and kidney, against hypoxic damage.

Hif-1α and its targets are generally considered mediators of late preconditioning versus early preconditioning in the heart. This idea was supported by earlier findings that showed that de novo protein synthesis was not required for IPC. These results have since been challenged by other studies that demonstrated an opposite outcome. In concordance, Cai et al recently showed that mice heterozygous for Hif-1α fail to exhibit early preconditioning, while Eckle et al reported that knockdown of Hif-1α abolished the effect of early ischemia preconditioning. But the mechanism for Hif-1α-mediated early preconditioning remains obscure. Since early preconditioning occurs immediately after brief episodes of hypoxia/reoxygenation, it is unlikely that it involves transcriptional events. Indeed, Rowland et al showed that de novo mRNA synthesis is not required for IPC. Interestingly, immunostaining of the myocytes for Hif-1α revealed its preferentially localization to the cytosol in a punctate appearance, but only during HPC or miR-199a eraser treatment. It was thus predicted, and, later, confirmed that it associates with mitochondria under these conditions. Although it is unclear what its role there may be, it is known now that it is required for HPC-mediated mitochondrial protection (FIG. 4b).

Example 3

Mi-R-21

Materials and Methods

Cell cultures and adenovirus Infection—Neonatal cardiac myocytes were prepared from Sprague Dawley rat hearts as previously described, using both pre-plating and percoll gradients for enriching of myocytes. Adult cardiac myocytes were prepared as previously described.

All exogenous recombinant DNA were delivered to the myocytes via recombinant adenoviruses using 10-20 multiplicity of infection.

Construction of adenoviruses—Recombinant adenoviruses were constructed, propagated and titered. The viruses were purified on a cesium chloride gradient followed by dialysis against 20 mM Tris buffered saline with 2% glycerol.

DNA Constructs cloned into recombinant Adenovirus—The stem-loop precursor of mmu-miR-199a-1 was synthesized and cloned into pDC316 vector under the control of a CMV promoter. For a negative control, a nonsense sequence was used in place of miR-199a, as previously described. The miR-199a-eraser is a tandem repeat of the anti-sense of mature miR-199a sequence, cloned into adenovirus vector under the regulation of a U6 promoter. Human Hif-1α (NM_001530.2) cDNA was purchased from Origene and cloned into the adenovirus vector. A mutant (Hif1αΔ199a) was constructed by excising nt 2761-2921 that encompass the miR-199a target sequence. Hairpin-forming oligonucleotides encompassing nt 2465-2485 of rat HIF1A (NM_024359) or nt 2211-2231 of mouse Sirt1 (NM_019812.1), were synthesized and cloned into adenoviruses.

Northern blotting—As previously described.

Cellular fractionation and Western blotting—Mitochondria was isolated using ProteoExtract Cytosol/Mitochondria Fractionation Kit (Calbiochem, NJ), according to the manufacturer's protocol. Fifteen μg of protein was separated on a 4% to 20% gradient SDS-PAGE (Criterion gels, Bio-Rad, CA) and transferred onto TransBlot Transfer membrane (Bio-Rad, CA).

The Antibodies used include: anti-Procaspase 12, anti-Caspase 9, anti-Caspase 6, and anti-GAPDH (Chemicon, MA); anti-cleaved Caspase 3 (Cell Signaling Technologies, MA), anti-BNip1 (B. D. Biosciences, CA), anti-Hif-1alpha (Novus Biologicals, CO), anti-p53 (Genscript, NJ), anti-H2B (Upstate biotechnology, MA), anti-actin (Santa Cruz), anti-cytochrome c (Santa Cruz Biotechnologies, CA), anti-iNOS (Ana Spec, CA), anti-Sir-2a (Upstate biotechnology, MA), anti-pHD2 (Novus Biologicals, CO), and anti-myosin-heavy chain (MHC) (Hybridoma Bank, University of Iowa, 10).

Hypoxia and Hypoxia Preconditioning (HPC)—Cultured myocytes were subjected to anoxia in a hypoxic chamber (Billups-Rothenberg Inc., CA). The chamber was filled with gas mixture of 95% N and 4.8%±0.2% CO2 (Inhalation Therapy, NJ) at 7 psi/12,000 kPa filling pressure for 15 minutes. The chamber was then placed in a 370 C incubator. For hypoxia preconditioning, cultured myocytes were subjected to anoxia/reoxygenation for 4×1 hour cycles.

Luciferase assay—A concatamer of miR-199a-predicted target sequence within the HIF1A 3'-UTR (GTTGGTTATTTTTGGACACTGGT(SEQ ID NO: 1))×3, the SIRT1 3'-UTR (GGACAGTTAACTTTTTAAACACTGG(SEQ ID NO: 2))×3, or a mutant sequence lacking any complementarity with miR-199a seed sequence, as previously described, were cloned in the 3'UTR of the luciferase gene driven by CMV promoter, generating Luc.Hif13'UTR, Luc.Skt13'UTR, and Luc.control vectors, respectively. Myocytes were transfected with these constructs, using Lipofectamine (Invitrogen, CA), in the presence or absence of virally-delivered miR-199a. After 24 h luciferase activity was assayed using an Lmax multiwell luminometer.

Caspase assay—Caspase-3 activity was measured using ApoTarget Caspase-3 Protease Assay (Biosource, Invitrogen, CA), as recommended by the manufacturer. The activity was normalized to total protein content.

Immunocytochemistry—As previously described 31. The Antibodies used include: anti-Hif-1alpha (Novus Biologicals, CO), anti-p53 (Genscript, NJ), and anti-myosin-heavy chain (MHC) (Hybridoma Bank, University of Iowa, 10).

Monitoring mitochondrial membrane potential—Mitochondrial Membrane potential was monitored using JC-1 cationic dye (Molecular Probes, Invitrogen, CA) as recommended by the manufacturer. Briefly, the cells were incubated with JC-1 (0.35 ug/ml) for 20 mins at 370 C. The cells were then washed with 1×PBS and imaged live.

Cardiac ischemia in C57Bl/6 mice—Through a left 3rd intercostal thoracotomy the pericardial sac is opened and an 8-0 nylon suture is passed under the left anterior descending coronary artery 2-3 mm from the tip of the left auricle. Then a nontraumatic silicone tubing is placed on top of the vessel and a knot tied on top of the tubing to occlude the coronary artery and to induce a permanent occlusion.

Early ischemia preconditioning (IPC) of porcine hearts (first window)—IPC was induced by 2 cycles of 10 min coronary artery occlusion followed by 10 min of reperfusion.

Statistical Analysis—Calculation of significance between 2 groups was performed using an unpaired, two-tailed, t-test.

Results

Figure 7:
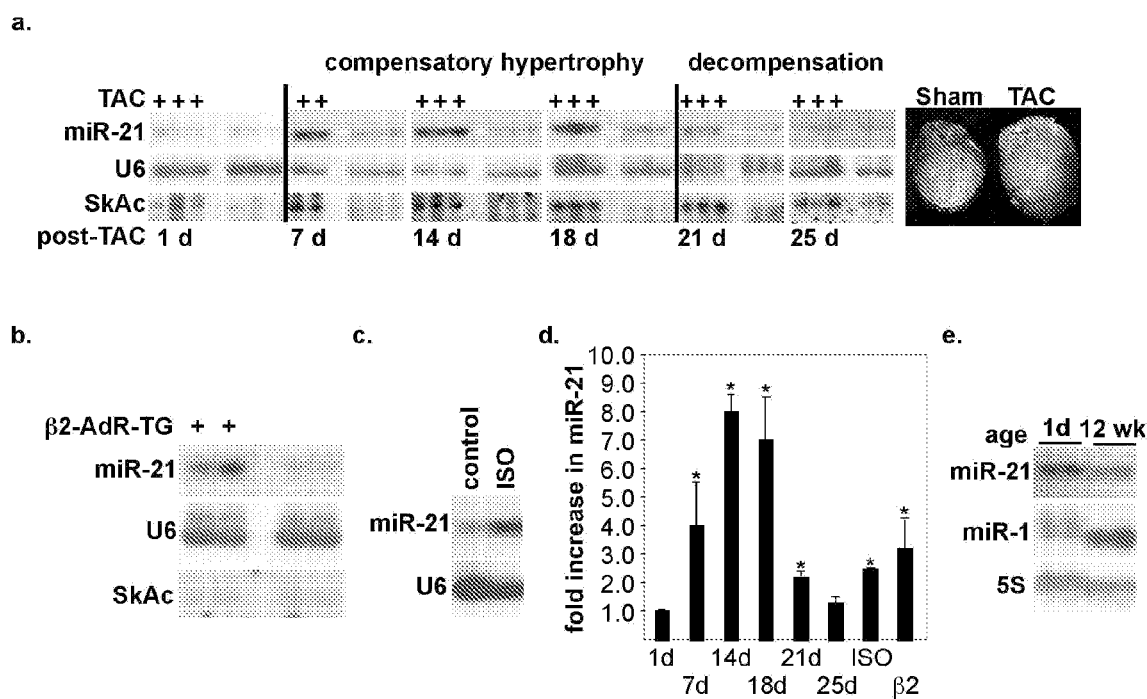
FIG. 7 shows Mir-21 is upregulated during cardiac hypertrophy.

MiR-21 is Upregulated During Cardiac Hypertrophy and Through Stimulation of the β-Adrenergic Receptor An array of microRNAs including miR-21 that was upregulated during cardiac hypertrophy was previously reported. MiR-21 increases by 4±1.5 and 8.3±0.6 fold, at 7 and 14 day, respectively, post-induction of hypertrophy using transverse aortic constriction (TAC) versus a sham operation in a mouse model (FIG. 7a). This was associated with 27±6% and 35±5% increase in heart/body weight, respectively, and an increase in skeletal actin, which is a marker of hypertrophy (FIG. 7a). The increase in miR-21 was sustained through 18 days post-TAC but started declining thereafter, concurrent with the onset of cardiac dysfunction (supplementary FIG. 7s). The levels of miR-21 in other genetic mouse models of cardiomyopathies were also assessed, the results of which revealed its upregulation in transgenic mice over-expressing β2-adrenergic receptor (β2AR) in the heart prior to development of any phenotype (FIG. 7b). βAR receptor stimulation plays a role in the development of cardiac hypertrophy, where studies have shown that infusion of its agonist, isoproterenol, increases cardiac contractility and hypertrophy in rodent models. It was confirmed that isoproterenol induces upregulation of miR-21 in isolated rat cardiocytes to almost the same extent as seen in the transgenic hearts (FIG. 7c-d). This suggests that the βAR receptors are upstream regulators of miR-21. MiR-21, which is ubiquitously expressed in adult human and mouse tissue, is relatively low in the normal adult heart, consistent with the sham-operated hearts seen in FIG. 7 (FIG. 7e). It is developmentally regulated, which in contrast to the muscle specific miR-1 is higher in the neonatal heart, which is known to grow though a process of cardiocyte hypertrophy (FIG. 7f). Thus, an increase in miR-21 accompanies hypertrophic growth, with the βAR receptor being one of its upstream regulators.

MiR-21 Targets sprouty2 and Induces Cellular Outgrowths

Figure 8:
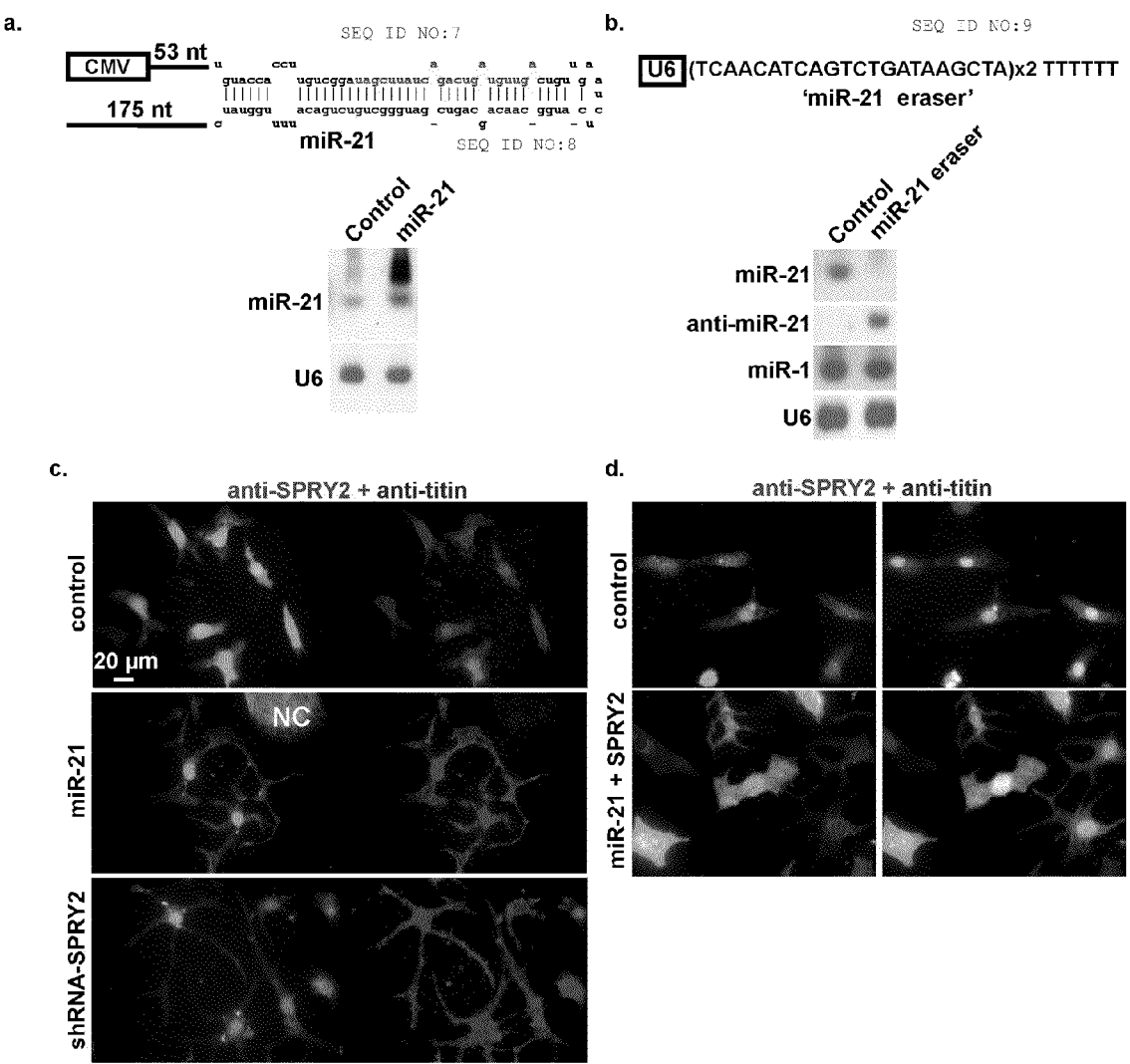
FIG. 8 shows Mir-21 induces cardiocyte outgrowth and down-regulation of SPRY2.

In order to address the role of miR-21 in cardiocytes a 320 nt sequence that encompasses the miR-21 stem-loop was cloned into a recombinant adenovirus (FIG. 8a). A tandem repeat of the anti-sense sequence of mature miR-21 was also cloned under the control of the U6 promoter (FIG. 8a). Northern blots analysis of cardiocytes treated with the former vector exhibit ~3 fold higher mature miR-21 versus control, although the premature construct accumulated at much higher levels, reflecting a rate limiting step in the processing of miR-21 (FIG. 8b). On the other hand, the anti-sense miR-21 was highly expressed and resulted in knockdown of endogenous miR-21, but not miR-1, to the extent that it was undetectable by Northern blotting (FIG. 8b). For that reason this construct was dubbed 'miR-21 eraser'.

Over-expressing miR-21 in cardiocytes did not influence hypertrophic growth in the absence or presence of growth factors as monitored by [3H]leucine incorporation (data not shown). But after 48-72 h in culture extensive cellular outgrowths (4±3 branches/cell) were noticed that varied in length (44±28 µm) depending on the distance between neighboring cells (FIG. 8c). Sprouty, a known inhibitor of branching morphogenesis and neurite outgrowth, is predicted to be a miR-21 target by TargetScanS and PicTar miRNA target prediction software, each using a unique set of algorithms. To confirm its potential in mediating miR-21's branching effects, it was independently knocked down using adenoviral delivered short-hairpin RNA (see FIG. 8e). This elicited even more impressive cardiocyte outgrowths, which suggested that miR-21's effect might be mediated through this putative target (FIG. 8c).

Using Western blot analysis down-regulation of endogenous SPRY2 (52±4%) was confirmed upon over-expression of miR-21 for 48 hr (FIG. 8d). Since sprouty negatively regulates erk1/2, phospho-erk1/2 was used as a marker for monitoring changes in Spry2 function that would be regulated by changes in its levels. The results of this show that down-regulation of SPRY2 by miR-21 or shRNA (67±9%) is accompanied by an increase in basal phosph-erk1/2 by 5±1.5 and 1.5±0.15 fold, respectively. In contrast, over-expression of SPRY2, or knockdown of miR21 using the miR-21 eraser, resulted in partial inhibition of fetal bovine serum-induced phosphoerk1/2 (FIG. 8f-g). Thus, SPRY2 is a downstream target of miR-21 (could be a direct or indirect target at this juncture) and has limiting cellular concentrations.

Figure 9:
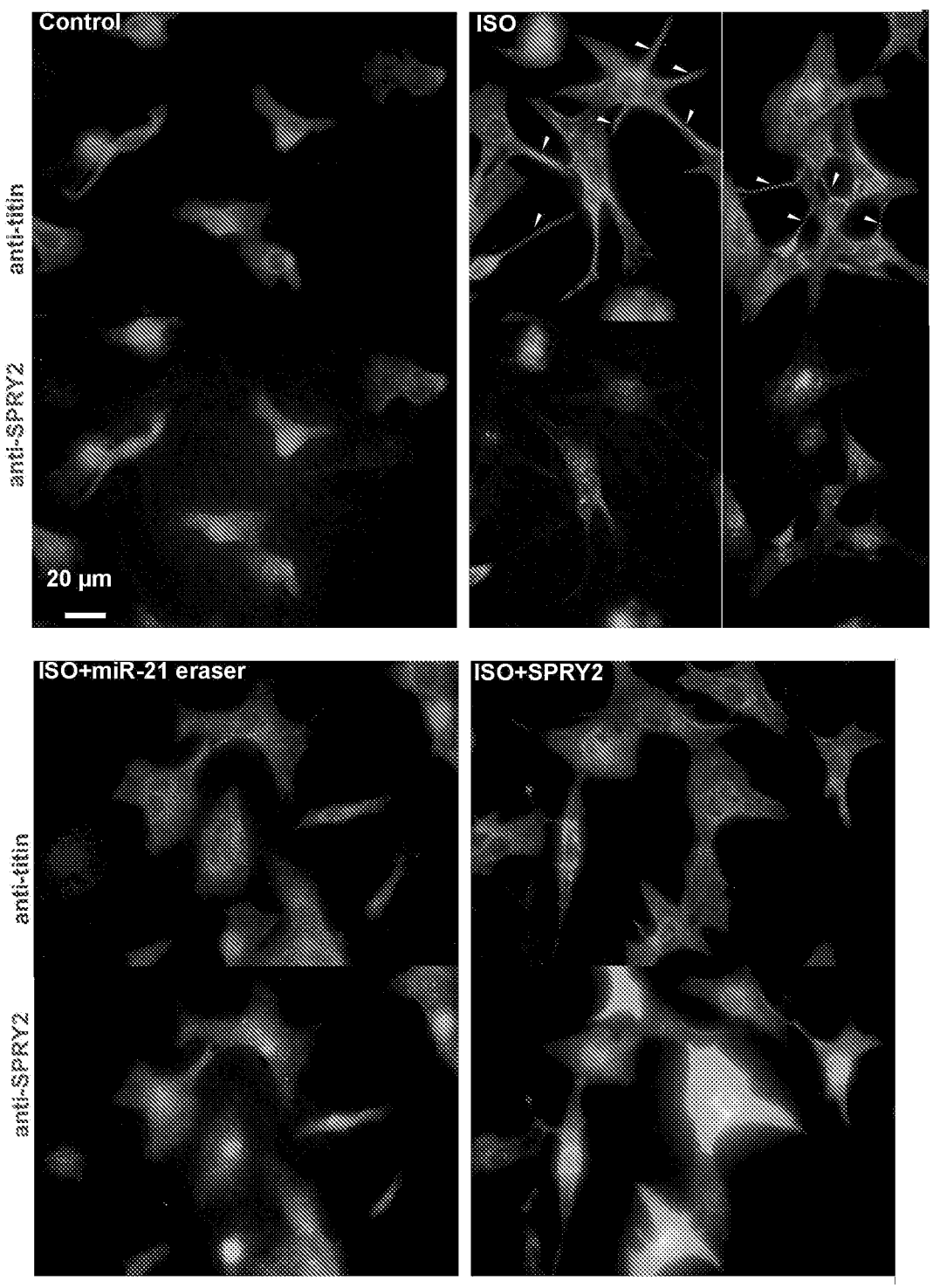
FIG. 9 shows β-Adrenergic receptors induces cellular outgrowths and down-regulation of SPRY2 in cardiocytes.

To determine if SPRY2 is a direct target of miR-21, the miR-21 predicted target sequence that is contained within its 3'UTR was cloned, downstream of a luciferase gene (Luc.SPRY2, FIG. 8h). This sequence conferred miR-21-induced inhibition of the luciferase activity by 76±4% (FIG. 8h). For confirming specificity, a mutated miR-21 SPRY2 target sequence was cloned, in which the seed-binding sequence was completely altered (Luc.mtSPRY2), downstream of the luciferase gene. As seen in FIG. 8h, not only did this abolish the effect of exogenous miR-21 on the reporter, but it also relieved it from inhibition by the endogenous miR-21. Thus, it was concluded that SPRY2 is a direct target of miR-21.

β-Adrenergic Receptor Stimulation Induces Down-Regulation of SPRY2, which is Accompanied by Cell-to-Cell Connecting Cellular Outgrowths The physiological relevance of these miR-21-induced outgrowths were assessed. After treatment of the cells with isoproterenol and staining them with an antibody against the sarcomeric protein titin, cellular outgrowth that were connecting or reaching out to adjacent cells was observed (FIG. 9a). The striated pattern of titin staining reflects the presence of sarcomeres even within these branches. This effect was wide spread in all observed fields (4±3 branches/cell). Impressively, these outgrowths were abrogated by the miR-21 eraser or over-expression of SPRY2 (FIG. 9a). Co-immunostaining the cells with anti-SPRY2 reveals that SPRY2 is depressed in the presence of isoproterenol but restored in the presence of the miR-21 eraser or exogenous SPRY2. Similar results were obtained when cells were treated the a virus over-expressing β2AR (supplementary FIG. 9s). While FIG. 7 confirms that isoproterenol and β2AR induce upregulation of miR-21, FIG. 9b confirms that they also induce 70±22% downregulation of SPRY2 protein (FIG. 9b). Thus, cell-cell connecting cardiocyte outgrowths are a morphological change that accompanies βAR stimulation and is mediated by miR-21 through down-regulation of SPRY2.

Cellular Outgrowths Connect to Cardiocytes Via Gap Junctions

Figure 10:
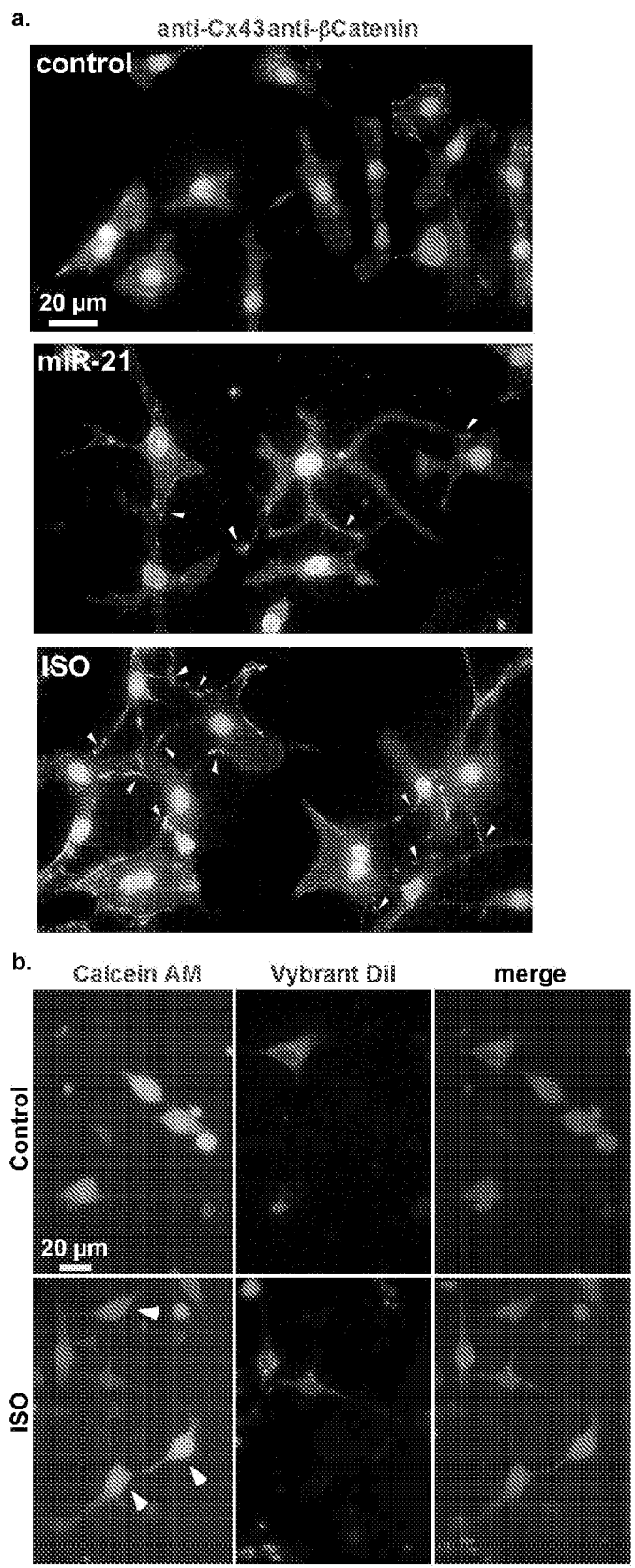
FIG. 10 shows cardiocyte outgrowths connect cells via gap junctions.

To verify the type of cell-cell connections conferred by these outgrowths Ad.miR-21- or isoproterenol-treated cardiocytes was immustained with anti-connexin43 (Cx43) and anti-βcatenin for detection of gap or adherens/tight junctions, respectively. Isoproterenol induced redistribution of Cx43 and βcatenin where they became distinctly localized at the points of contact with cell outgrowths (FIG. 10a). It appears that Cx43 alone is more prevalent at points of contact (white arrowheads), where βcatenin was occasionally found to co-exist (yellow arrowheads). On the other hand, while miR-21 induced outgrowths, minimal Cx43 or βcatenin could be seen at the contact sites, leading to the conclusion that additional factors induced by isoproterenol are required for Cx43 redistribution.

To test the functionality of these gap junction connections, two groups of cardiocytes, one loaded with cytosolic calcein AM (green) and the other labeled with the membrane dye Vybrant DiI (red) were co-plated. This approach enables us to distinguish any cells that might acquire calcein AM de novo from the originally loaded cells. While the untreated cells show 2 distinct single color populations of cells, after treatment with isoproterenol Vybrant DiI labeled cells (red arrowheads) were identified that have acquired the green dye from an adjacent calcein-only positive cell (white arrowheads), where the transferring dye could also be seen in the connecting branch (FIG. 10b). Thus, interconnecting cardiocyte branches serve the purpose of conduction of molecules between cells.

Figure 11:
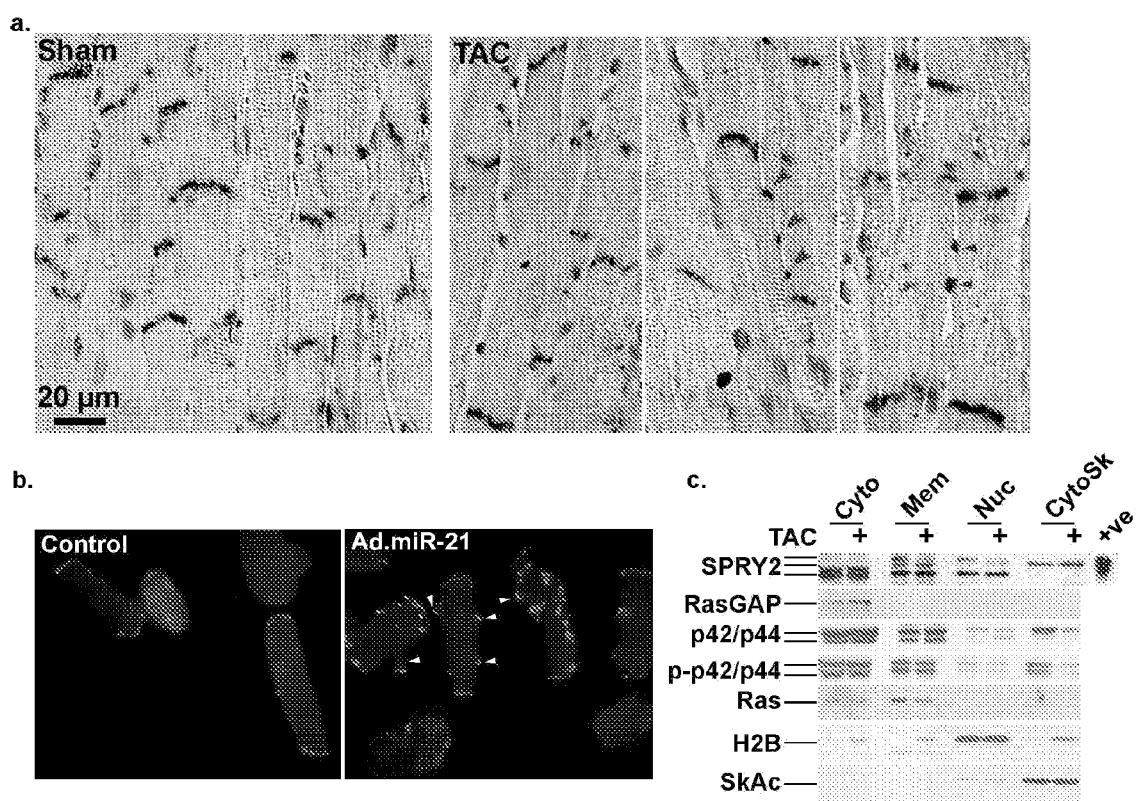
FIG. 11 shows cardiac hypertrophy is associated with connexin-43 positive side-branch connections and down-regulation of SPRY2.

Since the experiments described above were performed in neonatal cultured cardiocytes, which are generally more plastic, it was postulated how these outgrowths might develop in the morphologically uniform rod-shaped adult cardiocytes in vivo. For this purpose hypertrophied hearts from the TAC mouse model were sectioned and immunostained them with anti-Cx43. Compared to normal hearts, these showed connecting, short, lateral outgrowths between adjacent cardiocytes, where Cx43, which is normally strictly localized to the intercalated discs, demarcated the sites of contact (FIG. 11a). The figure shows three different depictions of these connections. To determine if miR-21 mediates this effect, normal adult cardiocytes that were treated with the miR-21-expressing adenovirus were isolated for 72 h. After immunostaining with antiCx43, Cx43-demarcated lateral protrusions (FIG. 11b, arrowheads) were observed. The levels of SPRY2 in the hypertrophied heart were also determined. The change in SPRY2 protein was only detected in the slower migrating form, both in the membrane and nuclear fractions, but was not associated with an increase in phosph-erk1/2 (FIG. 11c). Thus, the upregulation of miR-21 in the adult cardiocytes evokes a rudimentary form of the cellular outgrowths of that observed in the neonatal cardiocytes.

Figure 12:
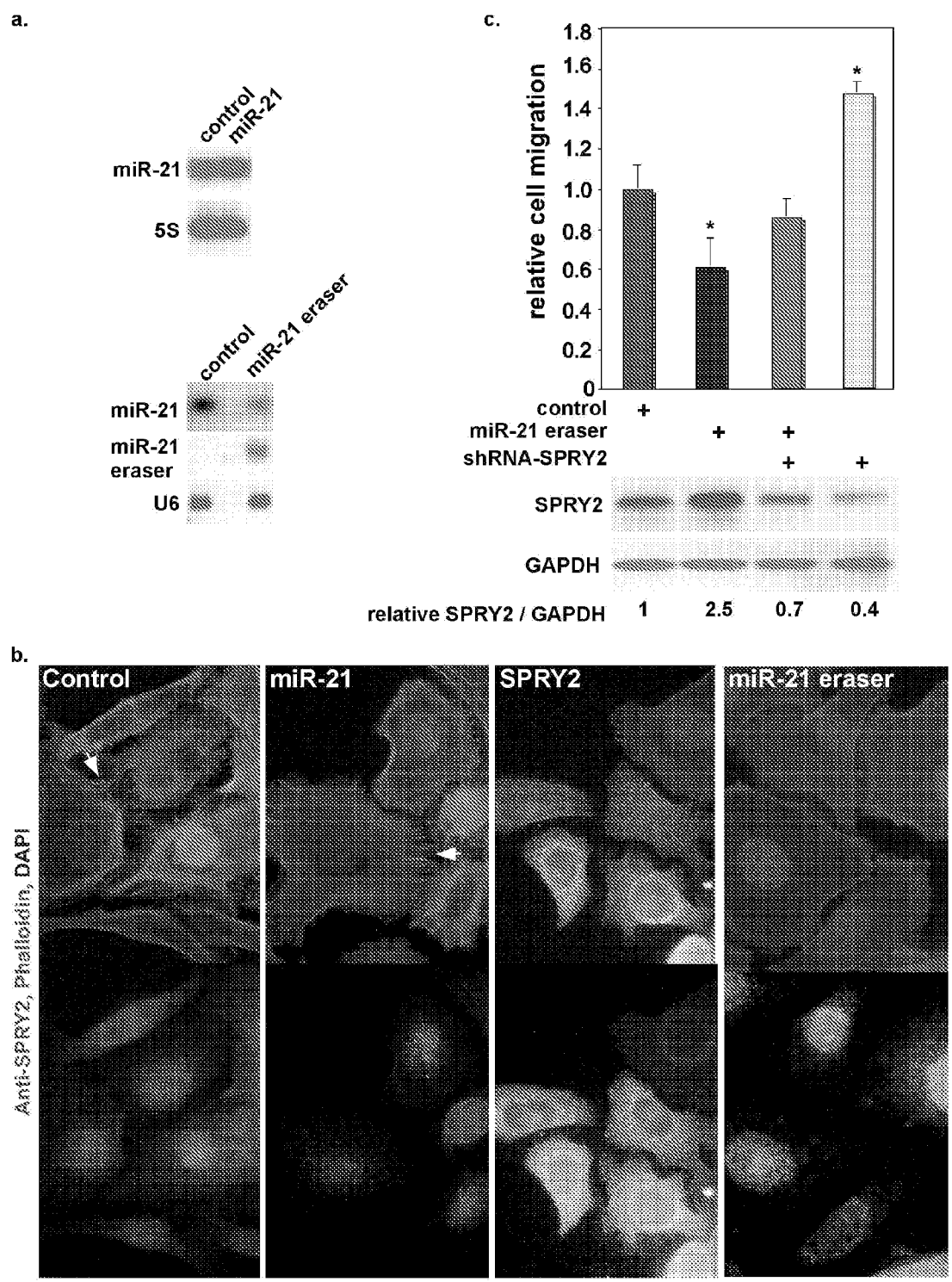
FIG. 12 shows over-expression of SPRY2 or knockdown of miR-21 in colon cancer cells abrogates formation of the microvilli-like protrusions.

Mir-21 Mediates the Formation of Microvillus-Like Protrusion in Colon Cancer Cells MiR-21 is over-expressed in many cancer forms. To determine how miR-21's effects seen in cardiocytes translate in cancer cells, it was over-expressed, SPRY2, or miR-21 eraser, in the colon cancer cells SW480. Over-expression of miR-21 results in minimal increase over the already very high endogenous levels, while miR-21 eraser results in ~70% reduction in endogenous miR-21 (FIG. 12a). Staining the cells with actin-binding phalloidin reveal microvillus-like protrusion that are enriched throughout the surface of the cell (FIG. 12b). Although further loading of these cells with exogenous miR- 21 results in no obvious change in cell morphology, SPRY2 and miR-21 eraser resulted in abrogation of the microvilli-like structures. Coimmunostaining the cells with anti-SPRY2 show more intense staining of SPRY2 in miR-21 eraser or SPRY2 over-expressing cells, as expected. The results suggest miR-21 and SPRY2 play a role in the formation of microvilli-like protrusions in colon cancer cells. This supports the role of miR-21 in cell metastasis.

Discussion

MiR-21, its Association with Cell Growth and its Upstream Regulators

Mir-21 has attracted more attention than any other miRNA, as it is one of the most highly upregulated in various cancers, cardiac hypertrophy, and neointimal formation, suggesting that it has a fundamental role in cell growth. In agreement, its level is fairly higher in the neonatal vs. adult heart, where it is upregulated upon induction of hypertrophic growth. On the other hand, its level starts declining with the onset of cardiac failure, ultimately dropping to basal levels. This also coincides with down-regulation and desensitization of the βARs. Moreover, β2AR-over-expressing mice exhibit upregulation of miR-21 in the heart, while isoproterenol stimulation of cultured cardiocytes induces upregulation of miR-21, down-regulation of SPRY2 and enhanced myocyte branching. Collectively, these data suggest that βARs are upstream regulators of miR-21 in the heart. Interestingly, it was recently reported that stress mediated through βAR stimulation enhances ovarian cancer cell invasiveness. Thus, it is also plausible that βAR also plays a role in enhancing miR-21 in cancer cells, where it may induce upregulation of miR-21, down-regulation of SPRY2, and increase microvilli and, thereby, cell migration.

Evidence Supporting a Role for βAR in Inducing Cardiocyte Connectivity and its Association with Cardiac Hypertrophy In support of a role for βAR stimulation in cell-cell connections and conduction, it was recently reported to increase the expression of connexin43 and conduction velocity in cultured neonatal cardiocytes. Conduction velocity, which is partly regulated by the abundance of gap junctions, is increased during early hypertrophy but decreased during later decompensation stages, which coincides with the decline in βARs and connexin43. Similarly, stretch and cAMP, induce upregulation of connexin43 and gap junction density in parallel with an increase in conduction velocity in cultured cardiocytes. These data reconcile well with our results in FIG. 3a showing extensive interconnecting cellular branches induced by isoproterenol treatment of isolated cardiocytes.

Cardiocytes adjacent to infarct zones or those subjected to aortic banding-induced hypertrophy or pulmonary hypertension-induced hypertrophy, exhibit extensive remodeling of gap junctions. This remodeling is in the form of punctate distribution of connexin43 throughout the perimeter of the cell, which is normally confined to its end intercalate discs. This is similar to its diffuse distribution in neonatal heart cardiocytes. Interestingly, a similar pattern of connexin43 labeling after TAC and in isolated adult cardiocytes over-expressing miR21 was observed (FIG. 11b). It is proposed that the lateralization of connexin43 demarcate sites of cell-to-cell connecting branches, which are induced by upregulation of miR-21 and down-regulation of its target SPRY2. Similarly, in normal human hearts connexin43 is predominantly (91.7%) restricted to the intercalated discs. During early stages of cardiac hypertrophy connexin43 is increased by 44.3%, but only 60.3% is localized to intercalated discs while more of the protein appears on the lateral sarcolemma. But during later stages of hypertrophy and decompensation, connexin43 levels are reduced and the lateral distribution disappears. This distribution and expression profile of connexin43 agrees with a scenario in which increased miR-21 during compensatory hypertrophy is associated with increased Cx43positive, cell-cell connecting side branches, which is reversed during failure commensurate with the decline of miR-21.

The Role of SPRY in Branching and Cancer

Sprouty was first discovered as an inhibitor of FGF signaling and branching of *Drosophila* airways. This effect is conserved as shown by knockdown of SPRY2 in mouse lungs. Sprouty inhibits MAPK activation by fibroblast growth factor (FGF) and endothelial growth factor (EGF). Inhibition of branching is not restricted to the lungs, but SPRY2 also inhibits ureteric, as well as, chorionic vellous branching and reduces trophoblast cell migration. Although the branches referred to here are tubular multicellular structures that underlie organogenesis, they are initiated by single cell sprouting. But most relevant to this study, is inhibition of neurite outgrowths by SPRY2.

A previous report shows that spouty1 was upregulated after unloading of a human heart, which agrees with the finding of the present invention that SPRY2 is down-regulated during hypertrophy. SPRY was also found in vascular endothelial cells and has been shown to inhibit vasculargenesis. Likewise, sprouty4 inhibits FGF and vascular endothelial growth factor (VEGF)-induced endothelial cell migration and proliferation, while SPRY2 inhibits migration and proliferation of smooth muscle cells. This reconciles well with the observed upregulation of miR-21 during neointimal formation, which has been shown to enhance smooth muscle proliferation, and our discovery of SPRY2 being one of its targets.

Sprouty is down-regulated in prostrate cancer, breast cancer, hepatocellular carcinoma, and non-small cell lung cancer. While independently, it was shown that these forms of cancer are also associated with upregulation of miR-21. Like down-regulation of SPRY2, upregulation of miR-21 enhances cell proliferation and migration. This also agrees with a pathway in which upregulated miR-21 targets and down-regulates SPRY2, thereby, enhancing proliferation and migration. But in addition, it has been shown that miR-21 can contribute to carcinogenesis through inhibition of apoptosis, or downregulation of other tumor suppressors, such as phosphatase and tensin homolog deleted on chromosome 10 (PTEN) and tropomyosin 1 (TPM1). The results of the present invention suggest that miR-21 through down-regulating SPRY2 may enhance metastasis through promoting the formation of microvilli.

The 'Eraser' is a Powerful Tool for Specific Knockdown of Endogenous miRNA

Inhibition or knockdown of a specific miRNA is key in understanding its function. For that purpose several approaches have been devised. Those include the 2'-O-methyl or LNA-modified oligoribonucleotides, and 'antagomirs', which have a phosphorothioate backbone, a cholesterol-moiety at 3'-end, and 2'-O-methyl modifications. In contrast to these transiently delivered oligonucleotides, it was recently reported the delivery of anti-sense miRNA sequence using expression vectors termed 'sponges'. The 'miRNA eraser' is similar in concept to the latter, but differs in the mechanism of inhibition of the miRNA. While the sponges induce a modest variable decrease of the endogenous miRNA the 'eraser' wipes it out. The loss of the miRNA signal on the Northern blots cannot be explained by competition of the complementary eraser RNA with the labeled miRNA probe used for the detection, since Northern blots are normally performed under extreme denaturing conditions. While it reduced endogenous miR-21 to undetectable levels in cardiocytes, it appeared less effective in cancer cells only because it was diluted out by the rapidly proliferating cultures. The eraser differs from the sponge in 2 physical aspects; one, the lack of stem-loop sequences at the 5' and 3' ends of tandem repeat sequence and, two, its delivery via a viral vector. Other plausible reasons for the difference in the outcome are the nature of the cell types or the targeted microRNA tested in both studies.

CONCLUSION

In conclusion, miR-21 plays a role in inducing the formation of cellular outgrowths that connect cardiocytes through gap junctions, which are usually confined to the intercalated discs in the normal adult heart. This change is provoked by βAR stimulation and mediated through down-regulation of SPRY2, an established negative regulator branching morphogenesis. It is proposed that this is an adaptive effect seen during cardiac hypertrophic growth and is associated with gap junction remodeling and enhanced conduction velocity but is reversed during cardiac failure. On the other hand, miR-21 promotes microvilli formation in colon cancer cells, which would potentially enhance extravasation and metastasis. It is also postulated that βAR stimulation may also induce upregulation of miR-21 and microvilli in cancer cells.

We claim:

1. An expression vector comprising a double stranded DNA, wherein the double stranded DNA comprises DNA complements of two repeats of at least one sequence of antisense miRNA complementary to miR-21, wherein said DNA complements consist of SEQ ID NO:9.

2. The expression vector of claim 1, wherein the DNA comprises and ApaI restriction sight-compatible overhang at the 5' end.

3. The expression vector of claim 1, wherein the DNA comprises a HindIII restriction site-compatible overhang at the 3' end.

4. The expression vector of claim 1, wherein the DNA comprises a stop sequence for RNA polymerase III.

5. The expression vector of claim 4, wherein the stop sequence for RNA polymerase III comprises a sequence of at least six deoxythymidine residues.

6. The expression vector of claim 1, wherein the expression vector comprises a U6 RNA polymerase III-dependent promoter.

7. A cell comprising an expression vector of claim 1.

8. An expression vector comprising a double stranded DNA, wherein the double stranded DNA comprises DNA complements of at least two repeats of SEQ ID No. 1 or SEQ ID No. 2.

* * * * *

```
                         SEQUENCE LISTING

<160> NUMBER OF SEQ ID NOS: 11

<210> SEQ ID NO 1
<211> LENGTH: 23
<212> TYPE: DNA
<213> ORGANISM: Mus musculus

<400> SEQUENCE: 1
gttggttatt tttggacact ggt                                             23

<210> SEQ ID NO 2
<211> LENGTH: 25
<212> TYPE: DNA
<213> ORGANISM: Mus musculus

<400> SEQUENCE: 2
ggacagttaa cttttttaaac actgg                                          25

<210> SEQ ID NO 3
<211> LENGTH: 23
<212> TYPE: RNA
<213> ORGANISM: Mus musculus

<400> SEQUENCE: 3
guugguuauu uuuggacacu ggu                                             23

<210> SEQ ID NO 4
<211> LENGTH: 24
<212> TYPE: RNA
<213> ORGANISM: Mus musculus
<220> FEATURE:
<221> NAME/KEY: stem_loop
<222> LOCATION: (16)..(16)

<400> SEQUENCE: 4
cuuguccauc agauusugug accc                                            24

<210> SEQ ID NO 5
<211> LENGTH: 26
<212> TYPE: DNA
<213> ORGANISM: Mus musculus

<400> SEQUENCE: 5
ggacagttaa cttttttaaac actggc                                         26

<210> SEQ ID NO 6
<211> LENGTH: 26
<212> TYPE: RNA
<213> ORGANISM: Mus musculus
<220> FEATURE:
<221> NAME/KEY: stem_loop
```

```
<222> LOCATION: (10)..(12)

<400> SEQUENCE: 6
cuuguccaus sscagauuug ugaccc                                    26

<210> SEQ ID NO 7
<211> LENGTH: 47
<212> TYPE: RNA
<213> ORGANISM: Mus musculus

<400> SEQUENCE: 7
uguaccaccu ugucggauag cuuaucagac ugauguugac uguugaa              47

<210> SEQ ID NO 8
<211> LENGTH: 47
<212> TYPE: RNA
<213> ORGANISM: Mus musculus
<220> FEATURE:
<221> NAME/KEY: stem_loop
<222> LOCATION: (27)..(27)
<220> FEATURE:
<221> NAME/KEY: stem_loop
<222> LOCATION: (39)..(39)
<220> FEATURE:
<221> NAME/KEY: stem_loop
<222> LOCATION: (44)..(44)

<400> SEQUENCE: 8 cuauggu uuu acagucuguc ggguagscug acgacaacsg guascuc              47

<210> SEQ ID NO 9
<211> LENGTH: 50
<212> TYPE: DNA
<213> ORGANISM: Mus musculus

<400> SEQUENCE: 9
tcaacatcag tctgataagc tatcaacatc agtctgataa gctattttt            50

<210> SEQ ID NO 10
<211> LENGTH: 23
<212> TYPE: DNA
<213> ORGANISM: Mus musculus

<400> SEQUENCE: 10
ggagacccac attgcataag cta                                        23

<210> SEQ ID NO 11
<211> LENGTH: 23
<212> TYPE: DNA
<213> ORGANISM: Mus musculus

<400> SEQUENCE: 11
ggagacccac attgcgacta taa                                        23
```